United States Patent [19]

Wilke et al.

[11] 4,152,366
[45] May 1, 1979

[54] OPTICALLY ACTIVE 3-METHYL-PENTENE-1

[75] Inventors: Günther Wilke; Borislav Bodanovic; Horst Pauling, all of Mülheim, Ruhr, Fed. Rep. of Germany

[73] Assignee: Studiengesellschaft Kohle mbH, Mülheim, Ruhr, Fed. Rep. of Germany

[21] Appl. No.: 836,442

[22] Filed: Sep. 22, 1977

Related U.S. Application Data

[60] Division of Ser. No. 649,164, Jan. 14, 1976, Pat. No. 4,098,834, which is a continuation of Ser. No. 413,722, Nov. 7, 1973, Pat. No. 3,978,147, which is a continuation-in-part of Ser. No. 166,957, Jul. 28, 1971, abandoned.

[30] Foreign Application Priority Data

Aug. 6, 1970 [DE] Fed. Rep. of Germany ....... 2039125

[51] Int. Cl.² ............................................. C07C 11/10
[52] U.S. Cl. ...................................... 585/16; 568/821; 585/360; 585/365; 585/375; 585/513
[58] Field of Search .................................. 260/677 R

[56] References Cited

PUBLICATIONS

Klaus Naumann et al., J. Amer. Chem. Soc., 91 pp. 2788–2789, 1969.
Klaus Naumann et al., J. Amer. Chem. Soc., 91, pp. 7012–7023, 1969.
W. R. Moser, J. Amer. Chem. Soc., 91, pp. 1137–1138, 1969.

*Primary Examiner*—Veronica O'Keefe
*Attorney, Agent, or Firm*—Sprung, Felfe, Horn, Lynch & Kramer

[57] ABSTRACT

Optically active compounds are prepared from optically inactive unsaturated hydrocarbons by reacting at least one unsaturated hydrocarbon in the presence of a catalyst prepared by combining a nickel compound, a Lewis acid and an optically active phosphine of the general formula $$PR'R''R'''$$

in which R', R" and R''' are hydrocarbon radicals, thereby forming optically active compounds having chiral centers formed by the carbon-to-carbon linkages. The optically active compounds can be polymerized to provide optically active polymers.

1 Claim, No Drawings

OPTICALLY ACTIVE 3-METHYL-PENTENE-1

RELATED APPLICATION

This is a division of Ser. No. 649,164 filed Jan. 14, 1976 now U.S. Pat. No. 4,098,834 which is a continuation of application Ser. No. 413,722 filed Nov. 7, 1973 now U.S. Pat. No. 3,978,147 which in turn is a continuation-in-part of application Ser. No. 166,957 filed July 28, 1971, now abandoned.

BACKGROUND

This invention relates to a process for the preparation of optically active carbon compounds.

The process relates to the preparation of optically active carbon compounds from optically inactive hydrocarbons, with development of the chiral centers by the carbon-to-carbon linkages.

Chemical literature reveals only three examples of non-enzymatic, asymmetrical catalysis by way of C—C linkage. J. Furukawa et al. (*Bulletin of the Chemical Soc. of Japan*, Vol. 41, 155 (1968) describe the synthesis of optically active trimethyl cyclododecatrienes from pentadi-1,3-ene, using a catalyst of titanium tetra-menthozyl and diethyl aluminium monochloride at 40° C. However, insufficient information is given regarding the yield of the optically active products and their optical purity and according to the indicated data, the yields are not higher than 10% and 4%, respectively. The authors themselves point out that the optical purities cannot be high, since the rotations are small.

H. Nozaki et al (*Tetrahedron* Vol. 24, 3655 (1968) obtained trans-1-methyl-2-phenylcyclopropane from diazomethane and 1-methyl-2-phenyl-ethylene with a yield of optical product of less than 8% at 60° C., with the aid of a catalyst consisting of an optically active cupric complex. Cuprous chloride catalysts with complex-bonded trialkyl or triaryl phosphite ligands were used by W. R. Moser (*J. Amer. Soc.* 91:15, 1135 (1969) for the synthesis of optically active cyclopropane derivatives from ethylene diazocetate and styrene. The ((−)-tribornyl-phosphite)-cuprous chloride produced the corresponding cyclopropane derivative with an optical yield of about 3% at 30° to 60° C.

The optical purities of the compounds produced by the above methods are unsatisfactory, because, firstly, the inducing groups on the catalyst are exchanged during the reaction for inactive groups and, secondly, the reactions mentioned in the examples only proceed at relatively high temperatures.

SUMMARY

It has now been found that optically active carbon compounds can be prepared from optically inactive hydrocarbons with C—C linkage and have optical purities which hitherto could not be produced by any catalytic process.

The invention therefore provides a process for the preparation of optically active carbon compounds from optically inactive unsaturated hydrocarbons which comprises reacting at least one unsaturated hydrocarbon in the presence of a catalyst prepared by combining at least one nickel compound, at least one Lewis acid and an optionally active phosphine of the general formula PR'R"R'" in which R', R" and R'" are hydrocarbon radicals.

DESCRIPTION

The catalysts known from the literature, as described above, are unable to combine two different unsaturated hydrocarbons to develop optically active centers.

The optically inactive starting compounds suitable for the synthesis are unsaturated hydrocarbons, such as open-chain, or cyclic olefins containing at least one double bond, wherein chiral centers can be formed by the carbon-to-carbon linkages.

The catalysts are prepared from various compounds of nickel, such as π-allyl-Ni-X of the general formula

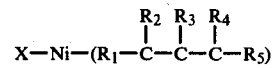

in which X is a chlorine, bromine or iodine atom, $R_1$ to $R_5$ are alkyl, aralkyl or aryl radicals or hydrogen atoms and any two radicals can be linked together to form a ring, or nickel -II-compounds, such as nickel hydroxide, nickel sulphide, nickel chloride, nickel cyanide, nickel bromide, nickel iodide, nickel carbonate, nickel formate, nickel acetate, nickel oxalate, nickel benzoate, nickel acetylacetonate, nickel acetoacetate ester, nickel benzoyl acetonate, nickel dimethylglyoxime, nickel oxide or nickel tetracarbonyl or even nickel-(0)- compounds, such as nickel tetraphenyl isonitrile, nickel tetra-p-bromophenyl isonitrile, nickel monocarbonyl-trimethyl isonitrile or nickel-bis-acrolein, nickel-bisacrylonitrile, nickel-bis-acrylonitrile, dipyridyl, nickel-bis-cimamic acid nitrile or bis-π-allyl nickel, bis-cyclooctadiene nickel.

The Lewis acids which may be particularly used are aluminum alkyls, aluminum alkyl halides or aluminum halides, such as aluminum trialkyls, dialkyl aluminum hydrides, dialkyl aluminum halides, alkyl aluminum sesquihalides, alkyl aluminum dihalides, dialkyl aluminum alkoxyls. It should be noted that if nickel-II-compounds are used, the Lewis acids must contain reducing groups.

Phosphines (PR'R"R'") are the ligands used to induce the optical activity according to the invention.

The radicals R', R" and R'" are hydrocarbon radicals preferably containing from 1 to 30 carbon atoms. Suitable hydrocarbon radicals include saturated, unsaturated, parafinic, naphthenic, olefinic, acetylenic and aromatic hydrocarbons.

The phosphines either contain the phosphorus atom as a chiral center, in which case R'R"R'" represents three different radicals which are bonded to the phosphorus and one of the enantiomers (*PR'R"R'") has been obtained by racemate cleavage, or in whicg optically active radicals R* are bonded to the phosphorus atom (PR*$_{3-n}$R$_n$). The combination of both types is also possible, so that phosphines with chiral phosphorus and optically active radicals, e.g., (*PR'R"R'"*) can be used.

Characteristic examples for the said three types are:

1. Phenyl-methyl-propyl-phosphine  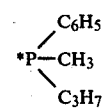

2. Tri-myrtanyl-phosphine 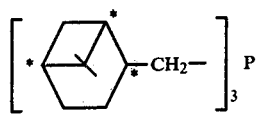

Menthyl-dimethylphosphine
Dimenthyl-methylphosphine
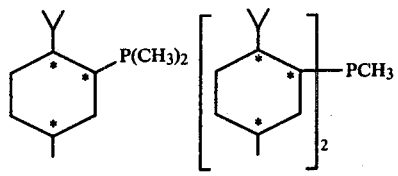

3. Menthyl-amyl-i-propylphosphine 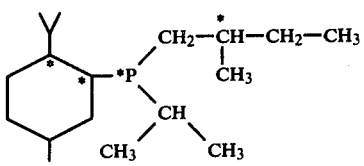

The phosphines of the second type can be prepared particularly easily but nevertheless highly active, since it is possible to make use of optically active natural products, without having to carry out the racemate cleavage operations. The best results obtained by the process of the invention are when the radicals R of the phosphines have a considerable steric bulk.

The process of the invention can be carried out within a wide temperature range, namely between approximately −120° and +100° C. The preferred reaction temperatures are between −78° and 0° C.

The reaction can take place at atmospheric pressure, or above atmospheric pressure and the reaction pressure is determined at the reaction temperature by the vapour pressure of the olefines and of the solvent being used.

The process can be carried out in an inert solvent, for example, chlorinated hydrocarbons, such as chlorobenzene or methyl chloride. It is recommended that carefully purified and anhydrous solvents should be used.

By means of the process according to the invention, it becomes possible to prepare optically active hydrocarbons by a catalytic procedure, which hydrocarbons contain functional groups in addition to the chiral carbon atoms, so that further conversions are possible, for example, the polymerization of optically active vinyl cyclooctene or 3-methyl-pentene-1(cf. Example 4-7 herein) provides optically active polymers.

Optically active polymers have improved physical (mechanical) properties because of their high steric regularity and have the ability to rotate the plane of polarized light.

Chromatography (qv) can be used to separate racemic mixtures into their antipodes employing optically active absorbants for this purpose.

Synthetic absorbants offer certain advantages, since their exchange properties and selectivity may be altered within broad limits. Optically active polymers have been used for separating enantiomers. Asymmetric functional groups have been introduced into insoluble polymers for this purpose. Alternatively, optically active components were condensed to yield insoluble resins to resolve enantiomers in this way.

Chromatography on a column filled with poly((S)-3-methyl-1pentene) results in the separation of poly((R) (S)-4-methyl-1-hexene) or poly(R) (S)-3-methyl-1-pentene) into levorotatory and dextrorotatory fractions.

Optically inactive crystalline poly(propylene oxide) may be separated into optically active fractions. In these cases one is not dealing, strictly speaking, with a separation of antipodes.

Optically active polymers such as soluble or crosslinked poly(S)-isobutylethylenimine) have been used as a catalyst for an asymmetric cyanohydrin synthesis, the optical yield being as high as 20%. The principle of using optically active polymers as asymmetric catalysts should be applicable to other syntheses as well. All enzymatic reactions and matrix-directed biosyntheses probably operate in this way. Autocatalysis in the preparation of optically active polymers is known.

An isotatic macromolecule can be synthesized by polymerizing (+)-propylene oxide with potassium hydroxide (JACS 78, 4787 (1958)). The feature of steroregularity is built into the monomer because all the monomer units have the same configuration as the asymmetric carbon. The polymer, in addition to being optically active, is a crystalline solid whereas the inactive polymer obtained by polymerizing (+)propylene oxide with potassium hydroxide is a liquid yet has approximately the same chain length (J. Polymer Sci. 34, 153 (1959)).

The reaction of the optically active vinyl cyclooctene with boron hydrides or aluminum hydrides, followed by oxidation and hydrolysis, yields, optically active cyclooctenyl ethyl alcohol. The alcohols of optically active 3-vinylcyclooctene have been found to differ extremely with respect to their fragrances. This behaviour of optically active compoubds is generally known in the perfume industry. For example, in Helvitica Chimica Acta, vol. 54 (1971) pages 1797 to 1801, it is disclosed that the optical antipodes of gama-citronellol cis- and trans- rose oxide, linalools and carvone differ in their respective fragrances. These discoveries led to a totally new source of compounds for the perfume industry involving selective optically active compounds.

It is also known from Angewandte Chemie, vol. 73 (1961) that beta(−)-citronellol has a fragrance similar to geranium oil whereas the (+)− product differs substantially in its fragrance.

A difference in properties is also exhibited between n-menthol and optically active 1-(n)-methanol. The latter compound has a different cooling effect on skin nerves in comparison with the optically inactive n-menthol. For this reason n-menthol is only half as costly as optically active 1-(n)-menthol. (*Pharmacie* 4 (1949) pages 224–226).

Because the process of the invention produces highly specific (optically) products, it is also possible to derive products of physiological interest which can be used as medicines.

The following Examples illustrate the invention.

Unless otherwise stated, all parts and percentages are by weight.

EXAMPLE 1

Ethylene at 1 atm was passed into a solution of 1.845 g (=10.25 m.mol) of $\pi$-allyl nickel bromide, 5.429 g )=12.30 m.mol) of (−)-tris(trans myrtanyl)-phosphine ($[\alpha]_D^{22}$ = −12.9°, c=1.710, $C_6H_6$; Mp. 51–52° C.) and 155.5 g (=1.44 mol) of cyclooctadi-1,3-ene in 300 ml of chlorobenzene at 0° C., with stirring until saturation had occurred. The catalytic reaction was started by adding a solution of 6.51 g (= 26.30 m.mol) of ethyl aluminum sesquichloride in 85 ml of chlorobenzene (within 10 minutes). The supply of ethylene at −5° to 0° C. was continued while stirring for 6 hours; thereafter the reaction was stopped by introducing gaseous ammonia into the solution at −30° C. The reaction mixture was then heated to 20° C., so that the main fraction of the ethylene dimers was evolved. The residual reaction product was separated from the catalyst by distillation under vacuum (0.2 or $10^{-4}$ mm.Hg).

Ethylene trimers (Bp. 52–70° C./760 mm/Hg), as well as chlorobenzene (Bp. 51–52° C./30 mm.Hg) and unreacted cyclooctadi-1,3-ene (Bp. 51–52° C./30 mm.Hg) were initially roughly separated on a Vigreux column; distillation was thereafter carried out on a 1-meter rotating band column and to obtain 17.7 g of a fraction of Bp. 78°–83.5° C./30 mm.Hg, $[\alpha]_D^{23.5}$ = −12.1° (c = 1.88, $C_6H_6$): consisting of 1.1% of cyclooctadi-1,3-ene, 0.2% of chlorobenzene, 89.0% of 3-vinyl clooctene, 8.0% of 3-ethylidene cyclooctene, cis and trans, as well as 39.9 g of a fraction of Bp. 83.5–111° C./30 mm.Hg, $[\alpha]_D^{25}$ = −0.9°(c=2.4, $C_6H_6$), with the composition: 3.4% of vinyl cyclooctene and 83.5% of cis and trans 3-ethylidene cyclooctene; the remainder consisted of olefines in the $C_{12}$ range. The distillation residue (29.3 g) $[\alpha]_D^{29}$ = −4.3° (c=7.92, $C_6H_6$), contained $C_{12}$ olefines and higher oligomers.

The 3-vinyl cyclooctene isolated in pure form by preparative gas chromatography showed a rotational value of $[\alpha]_D^{26.8}$ = −13.6° (c=3.82, $C_6H_6$), corresponding to an optical yield of 8–9%. The rotational value of the optically pure (−) 3-vinyl cyclooctene obtained by independent synthesis reactions and racemate cleavage was $[\alpha]_D^{25}$ = −162°°(c=4.8 $C_6H_6$).

EXAMPLE 2

Using the same process as in Example 1, to a solution of 0.310 g (=1.73 m.mol) of $\pi$-allyl nickel bromide, 0.879 g (=1.99 m.mol) of (−) tris(trans myrtanyl) phosphine and 26.0 g (=241 m.mol) of cyclooctadi-1,3-ene in 100 ml of chlorobenzene, in the presence of ethylene (1 atm), was added at −40° C. a solution of 1.062 g (=4.30 m.mol) of ethyl aluminum sesquichloride i 30 ml of chlorobenzene over a period of 1 hour. Ethylene was then passed for a further hour at −45° to −40° C., following by working up according to Example 1. The process yielded 3.5 g of a fraction of Bp. 78°–83.5° C./30 mm.Hg., $[\alpha]_D^{21.5}$ = −27.9°(c=8.28, $C_6H_6$), consisting of 4.0% of cyclooctadi-1,3-ene, 86.4% of 3-vinyl cyclooctene and 6.4% of cis and trans 3-ethylidene cyclooctene. The residue (4.9 g), $[\alpha]_D^{28}$ = −7.7°(c=5.43, $C_6H_6$), consisted of up to 44.5% of cis and trans 3-ethylidene cyclooctene and 55% of $C_{12}$ hydrocarbons and higher olefines. The 3-vinyl cyclooctene isolated in pure form showed a rotational value of $[\alpha]_D^{25}$ = −33.3° (c=8.44, $C_6H_6$), corresponding to an optical yield of 20–21%.

EXAMPLE 3

Using the same process as in Example 1, to a solution of 0.206 g (=1.52 m.mol) of $\pi$-allyl nickel chloride, 0.366 g (=1.83 m.mol) of (−) menthyl dimethylphosphine $[\alpha]_D^{25}$ = −119°; c=9.64, $C_6H_6$; Bp. 51° C./0.1–0.2 mm. Hg) and 29.6 g (=274 m.mol) of cyclooctadi-1,3-ene in 120 ml of chlorobenzene, in the presence of ethylene (1 atm) was added at 0° C., a solution of 0.95 g (=3.84 m.mol) of ethyl aluminum sesquichloride in 40 ml of chlorobenzene over a period of 15 minutes. Ethylene was passed for a further 6 hours at 0° C. into the solution and then the reaction mixture worked up. The process yielded 2.76 g of a fraction of Bp. 78°–83.5° C./30 mm.Hg with $[\alpha]_D^{25}$ = +7.8°(c=6.43 $C_6H_6$), consisting of up to 76.1% of 3-vinyl cyclooctene and 23.0% of cis and trans 3-ethylidene cyclooctene. From this, the rotational value of $[\alpha]_D^{25}$ = +10.2° for pure 3-vinyl cyclooctene (2.10 g) can be calculated and corresponds to an optical yield of 6–7%.

EXAMPLES 4–7

Separate solutions of 0.206 g (=1.52 m.mol) of $\pi$-allyl nickel chloride, 0.593 g (=1.83 m.mol) of dimenthyl methylphosphine $[\alpha]_D^{22}$ = −216°, (c=3.72, $C_6H_6$); Bp. 138° C./0.1–0.2 mm.Hg.) and 29.6 g (=274 m.mol) of cyclooctadi-1,3-ene in 120 ml of solvent were mixed with separate solutions of 0.94 g (=3.81 m.mol) of ethyl aluminum sesquichloride in 20 ml of solvent at different reaction temperatures (see Table 1) in the presence of ethylene. After 6 hours, working up was carried out according to Example 1. The $C_6$ fraction (ethylene trimers) contained inter alia the optically active 3-methylpent-1-ene (Bp. 54.3° C./760 mm.Hg), which was isolated by fine fractionation.

The reaction conditions, the solvents used, the yields of 3-methylpent-1-ene and 3-vinylcyclooctene, respectively, and also the optical yields are set out in Table 1:

TABLE I

| Example | Reaction temp. °C. | Solvent | 3-methyl-pent-1-ene | | | 3-vinyl cyclooctene | | |
|---|---|---|---|---|---|---|---|---|
| | | | Yield g | $[\alpha]_D^{22}$ | Optical[a] yield (%) | Yield g | $[\alpha]_D^{22}$ | Optical yield (%) |
| 4 | 0 | $C_6H_5Cl$ | 2.04 | +16.9 | 45.7 | 3.33 | −38.1 | 23–24 |
| 5 | −40 | " | 5.23 | +20.4 | 55.3 | 2.10 | −67.2 | 41–42 |
| 6 | −75 | $CH_3Cl$ | 1.73 | +17.1 | 46.3 | 0.25 | −86.0 | 53 |

TABLE I-continued

| | | | 3-methyl-pent-1-ene | | | 3-vinyl cyclooctene | | |
|---|---|---|---|---|---|---|---|---|
| Example | Reaction temp. °C. | Solvent | Yield g | $[\alpha]_D^{22}$ | Optical[a] yield (%) | Yield g | $[\alpha]_D^{22}$ | Optical yield (%) |
| 7[b] | −75 | " | 2.84 | +17.3 | 47.0 | — | — | — |

[a] calculated according to the rotational value for optically pure (+) 3-methyl-pent-1-ene (Lit: $[\alpha]_D^{17} = +36.9°$)
[b] preparation without cyclooctadi-1,3-ene

EXAMPLE 8

Using the same process as in Example 1, to a solution of 0.239 g (=1.75 m.mol) of π-allyl nickel chloride, 0.350 g (=2.11 m.mol) of optically active phenyl methyl-n-propylphosphine (K. Naumann, G. Zon, K. Mislow, J. Am. Chem. Soc. 91, 7012 (1969)) (characterised as phenyl methyl benzyl-n-propyl phosphonium bromide; Bp. 196°-202° C. $[\alpha]_D^{22} = -35.0°$; c=1.0, CH$_3$OH) and 28.3 g (=265 m.mol) of cyclooctadi-1,3-ene in 100 ml of chlorobenzene, in the presence of ethylene (1 atm) and at −40° C., was added a solution of 1.09 g (=4.38 m.mol) of ethyl aluminum sesquichloride in 10 ml of chlorobenzene within 5 minutes. Then ethylene was passed within 3 hours at −40° C. into the solution. The working up yielded 0.45 g of a fraction of Bp. 78°-82° C./30 mm.Hg., $[\alpha]_D^{25} = +17.3°$ (c=2.5, C$_6$H$_6$), consisting of 8.8% of cyclooctadi-1,3-ene and 89.9% of 3-vinyl cyclooctene. From this, for pure 3-vinyl cyclooctene, it was calculated that $[\alpha]_D^{25} = +19.25$, corresponding to an optical yield of 12%.

EXAMPLE 9

A solution of 1.15 g (=4.65 m.mol) of ethyl aluminum sesquichloride in 10 ml of chlorobenzene was added dropwise with stirring at −40° C. and within 15 minutes to a solution 0.480 g (=1.86 m.mol) of nickel acetyl acetonate, 0.945 g (=2.14 m.mol) of (−) tris(tris-myrtanyl)phosphine and 26.3 g (=244 m.mol) of cyclooctadi-1,3-ene in 100 ml of chlorobenzene. After saturating at −40° C. with propylene at 1 atm, the reaction mixture was heated to 0° C. and propylene introduced for a further 20 hours while stirring. The reaction was stopped by adding 10 ml of concentrated ammonia and the organic layer shaken (with access of air) with dilute hydrochloric acid, washed until neutral and dried with CaCl$_2$. Propylene dimers (15 g, Bp. 54°-72° C./760 mm.Hg) and chlorobenzene were roughly distilled off on a 0.7 meter Vigreux column, the distillation residue recondensed under high vacuum (bath temperature up to 50° C.) and thereafter further distillation effected on a 0.7 meter rotary band column. The process yielded 24.5 g of C$_{11}$ olefines (Bp. 98°-104° C./30 mm.Hg; $[\alpha]_D^{22} = 4.65°$, undiluted), consisting of 27.0% of 3-isopropenylcyclooctene, 57.5% of cis and trans-3-propyl cyclooctene and 12.5% of bicyclo-[6.0.3] undecene-2 and -3, as well as 4.40 g of a fraction of Bp. 104°-136° C./30 mm.Hg; $[\alpha]_D^{20} = 0.5°$, undiluted). The 3-isopropenyl cyclootene (in 78% purity) and bicyclo-[6.0.3]-undecene-3 (in 93% purity) showed rotational values of respectively $[\alpha]_D^{23} = 16.1°$ (c=7.4, pentane) and $[\alpha]_D^{25} = +4.7°$ (c=9.9, pentane).

EXAMPLE 10

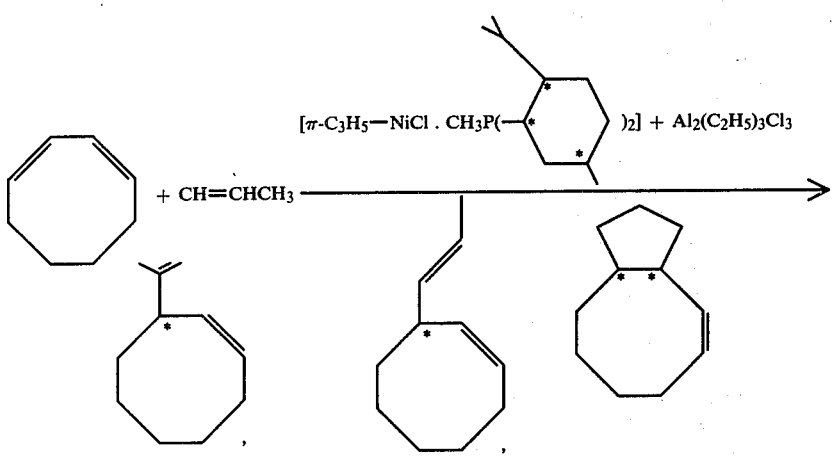

1.7 ml (=7.5 m.mol) of Al$_2$(C$_2$H$_5$)$_3$Cl$_3$ were added at −40° C. to 0.410 g (=3.0 m.mol) of π-allyl nickel chloride, 1.167 g (=3.6 m.mol) of (−) dimenthyl methyl phosphine ($[\alpha]_D^{25} = -214$, c=10.4, C$_6$H$_6$) and 57 ml (=450 m.mol) of cyclooctadi-1,3-ene dissolved in 150 ml of chlorobenzene and then propylene at 1 atm was passed through the solution at 0° C. for 20 hours with stirring. After that time, the catalytic reaction was stopped by introducing gaseous ammonia. All constituents which are volatile at 0.2 mm.Hg and at a bath temperature of 40°-50° C. were distilled over into a receiver cooled to −80° C. and, from the distillate, solvent and unreacted cyclooctadi-1,3-ene were distilled off at 30 mm.Hg. on a Vigreux column. By distillation on a 1 meter rotating band column, the process yielded 10.0 g of a C$_{11}$ fraction of Bp. 96°-102° C./30 mm.Hg and $[\alpha]_D^{25} = -83°$ (c=8.7, C$_6$H$_6$) of the composition:

56.2% of 3-isopropenyl cyclooctene,
11.6% of 3-propenyl cyclooctenes and
0.8% of bicyclooctenes
    (remainder unknown compounds)

EXAMPLE 11

| | (C₁₀H₁₈)₂PCH₃ + [π—C₃H₅NiBr]₂ + COD-1.5 + Al₂(C₂H₅)₃Cl₃ | | | |
|---|---|---|---|---|
| Molar ratio | 1,1 | 0,5 | 100 | 2 |
| COD-1.5 | 254 ml = | | 216 g = 1,997 Mol | |
| +[π—C₃H₅NiBr]₂ | | | 3,59 g = 9,99 mMol | |
| + (C₁₀H₁₈)₂PCH₃ | | | 7,07 g = 21,95 mMol, $[\alpha]_D^{25} = -214°$ (c=10, 4 g/ 100 ml Benzene) | |
| + Al₂(C₂H₅)₃Cl₃ | 9,17 ml = | | 9,9 g = 39,94 mMol | |

Dimenthyl-methyl-phosphine, π-allyl nickel bromide and cyclooctadi-1,5-ene were dissolved in 950 ml of methylene chloride and, when the mixture had cooled to 0° C., the solution of ethyl aluminum sesquichloride in 80 ml of methylene chloride was added dropwise. The reaction mixture was stirred for 144 hours at 0° C., whereafter the solvent and the C₈ hydrocarbons together with the ethyl aluminum sesquichloride were drawn off at room temperature under vacuum (mercury diffusion pump). The ethyl aluminum sesquichloride was destroyed by introducing gaseous ammonia, the solution was filtered and recondensed and the methylene chloride was distilled off through a Vigreux column.

Conversion: 99.0%.

C₈ hydrocarbons obtained: 221 ml=179 g=83%.

Rotary value of the C₈ mixture: = −1.2°

Composition of the C₈ hydrocarbon according to gas chromatography analysis:

bicyclo-[3.3.0]oct-2-ene: 92.5% by weight
cyclooctadi-1,3-ene: 3.6% by weight
cyclooctadi-1,4-ene: 1.9% by weight
bicyclooctene-Δ1.5: 0.7% by weight
cyclooctadi-1,5-ene: 1.0% by weight
residue: 0.3% by weight

EXAMPLE 12

Co-dimerization of norbornene and ethylene forming optical active (+)-exo-2-vinyl norbornane

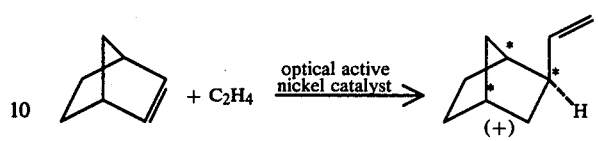

0.31 cc (1.33mmoles) ethyl aluminum sesquichloride were added to a solution of 0.18 g (1.33 mmoles) π-allyl nickel chloride and 0.562 g (1.6 mmoles) (−)-dimenthyl-isopropyl-phosphine in 150 cc methylene chloride at −70° C. under stirring. The mixture was saturated with ethylene at normal pressure and, then, into the mixture at that constant temperature and under current ethylene supply, a solution of 22.0 g (234 mmoles) norbornene in 60 cc methylene chloride was added dropwise during one hour. The ethylene feed was continued for further 5.5 hours at −70° C. after which the catalysis was interrupted by feeding gaseous NH₃ into the solution.

The volatile reaction products were separated from the catalyst residues and formed polymers by distillation in vacuum at a pressure of 0.2-0.4 Torr. The fractional distillation of the so isolated co-dimer resulted in 7.0 g of a fraction with boiling point 54° C./30 Torr which contains 97.6% of exo-2-vinyl norbornene having a rotational value of $[\alpha]_D^{22} = +37.4°$. The rotational value corresponds to an optical purity of 69.3% exo-2-vinyl norbornane.

Control 1

Attempted oligomerization of olefins using (tribornyl phosphite)-copper (I)-chloride-complex catalyst 2.46 g (5 mmole) (tribornyl phosphite)-copper(I)-chloride prepared according to W. R. Moser, J. Am. Chem. Soc. 91, 1135 (1969) (found: $\alpha_D^{25}=43.2°$ (c=2.48, benzene), according to Moser: $\alpha_D^{25}=47.8°$, melting point: 218° C. (according to Moser: 218° C.) were dissolved in 34.0 g (0.31 mole) cyclooctadiene-1,3. The reaction vessel, containing the mixture was evacuated and ethylene up to 1 atm. introduced. At 0° C. as well as at +30° C. there was no ethylene absorption. The cyclooctadiene-1,3 was isolated unchanged.

What is claimed is:

1. Optically active 3-methyl-pentene-1.

* * * * *

UNITED STATES PATENT AND TRADEMARK OFFICE
CERTIFICATE OF CORRECTION

PATENT NO. : 4,152,366
DATED : May 1, 1979
INVENTOR(S) : WILKE et al.

It is certified that error appears in the above-identified patent and that said Letters Patent are hereby corrected as shown below:

Title Page, Inventors, [75], "Bodanovic" should read
-- Bogdanovic --.

Column 2, line 2, "optionally" should read -- optically --.

Column 2, line 33, "bisacrylonitrile" should read
-- bis-acrylonitrile --.

Column 2, line 34, insert -- nickel-bis-fumaronitrile --
after "dipyridyl".

Column 2, line 35, "cimamic" should read -- cinnamic --.

Column 2, line 56, "whicg" should read -- which --.

Column 3, line 66, insert -- - -- after "1".

Column 4, line 43, "(+)" should read -- ($\pm$) --.

Column 4, line 53, "compoubds" should read -- compounds --.

Column 4, line 66, "methanol" should read -- menthol --.

Column 5, line 53, delete "°" second occurrence after "162°".

Column 6, line 4, "i" should read -- in --.

UNITED STATES PATENT AND TRADEMARK OFFICE
CERTIFICATE OF CORRECTION

PATENT NO. : 4,152,366
DATED : May 1, 1979
INVENTOR(S) : WILKE et al.

It is certified that error appears in the above-identified patent and that said Letters Patent are hereby corrected as shown below:

Column 7, line 58, "tris-" second occurrence should read -- trans- --.

Column 10, line 31, "norbornene" should read -- norbornane --.

Signed and Sealed this

Second Day of December 1980

[SEAL]

Attest:

SIDNEY A. DIAMOND

Attesting Officer    Commissioner of Patents and Trademarks